United States Patent
Björling et al.

(10) Patent No.: US 6,950,696 B2
(45) Date of Patent: Sep. 27, 2005

(54) METHOD AND CIRCUIT FOR DETECTING CARDIAC RHYTHM ABNORMALITIES BY ANALYZING TIME DIFFERENCES BETWEEN UNIPOLAR SIGNALS FROM A LEAD WITH A MULTI-ELECTRODE TIP

(75) Inventors: Anders Björling, Järfälla (SE); Sven-Erik Hedberg, Kungsängen (SE); Ulf Lindegren, Enskede (SE); Anders Lindgren, Täby (SE)

(73) Assignee: St. Jude Medical AB, Jarfalla (SE)

( * ) Notice: Subject to any disclaimer, the term of this patent is extended or adjusted under 35 U.S.C. 154(b) by 194 days.

(21) Appl. No.: 09/995,198

(22) Filed: Nov. 27, 2001

(65) Prior Publication Data

US 2003/0100923 A1 May 29, 2003

(51) Int. Cl.⁷ .............................................. A61B 5/046
(52) U.S. Cl. ........................ 600/515; 600/518; 128/923
(58) Field of Search ................ 600/509, 515, 600/518, 393; 607/9, 14, 25; 128/923

(56) References Cited

U.S. PATENT DOCUMENTS

| | | | | |
|---|---|---|---|---|
| 4,354,497 A | * | 10/1982 | Kahn | 607/5 |
| 4,754,753 A | * | 7/1988 | King | 600/512 |
| 4,913,146 A | * | 4/1990 | DeCote, Jr. | 607/9 |
| 4,955,382 A | * | 9/1990 | Franz et al. | 600/375 |
| 5,158,092 A | * | 10/1992 | Glace | 600/518 |
| 5,193,535 A | * | 3/1993 | Bardy et al. | 607/4 |
| 5,273,049 A | | 12/1993 | Steinhaus et al. | |
| 5,306,292 A | | 4/1994 | Lindegren | |
| 5,366,487 A | | 11/1994 | Adams et al. | |
| 5,385,146 A | * | 1/1995 | Goldreyer | 600/374 |
| 5,433,198 A | * | 7/1995 | Desai | 600/374 |
| 5,836,875 A | * | 11/1998 | Webster, Jr. | 600/374 |
| 6,064,905 A | * | 5/2000 | Webster et al. | 600/424 |
| 6,152,882 A | | 11/2000 | Prutchi | |
| 6,266,554 B1 | | 7/2001 | Hsu et al. | |
| 6,308,095 B1 | | 10/2001 | Hsu et al. | |
| 6,574,492 B1 | * | 6/2003 | Ben-Haim et al. | 600/374 |

FOREIGN PATENT DOCUMENTS

| | | |
|---|---|---|
| EP | 0 571 797 | 12/1993 |
| WO | WO97/12548 | 4/1997 |

\* cited by examiner

*Primary Examiner*—Kennedy Schaetzle
(74) *Attorney, Agent, or Firm*—Schiff Hardin LLP

(57) ABSTRACT

A circuit and method for detecting cardiac rhythm abnormalities employ unipolar signals respectively obtained from a cardiac lead having a tip at which a number of separate electrodes are disposed, the electrodes being simultaneously in contact with cardiac tissue. The respective unipolar signals which are obtained from the multiple electrodes exhibit a time relationship relative to each other, and this time relationship is analyzed to determine whether a cardiac rhythm abnormality is present or one or more of the unipolar signals is compared to a template which is known to represent a cardiac abnormality. Analysis of the time relation is undertaken by determining the absolute value of a time offset between any two of the unipolar signals, or by correlating any two of the unipolar signals.

38 Claims, 9 Drawing Sheets

METHOD AND CIRCUIT FOR DETECTING CARDIAC RHYTHM ABNORMALITIES BY ANALYZING TIME DIFFERENCES BETWEEN UNIPOLAR SIGNALS FROM A LEAD WITH A MULTI-ELECTRODE TIP

BACKGROUND OF THE INVENTION

1. Field of the Invention

The present invention is directed to a cardiac lead suitable for use in pacemakers, cardioverters, defibrillators, and the like, as well as to a method and circuit for using such a lead to detect cardiac rhythm abnormalities, such as fibrillation and tachycardia.

2. Description of the Prior Art

A cardiac lead typically has a proximal end with a connector adapted for electrical and mechanical connection to a cardiac-assist device, such as a pacemaker, cardioverter or defibrillator, and an opposite distal end, at which one or more electrodes is/are located. Between the distal end and the proximal end, the lead has a flexible insulating sheath or jacket, containing one or more conductors, depending on the number of electrodes.

The electrodes are exposed conductive surfaces at the distal end of the lead. Conventional electrode configurations include a unipolar configuration and a bipolar configuration. In a unipolar configuration, there is only one electrode at the distal end, typically a hemisphere covering the distal tip. Typically the housing, or a portion thereof, of the cardiac assist device is used as the indifferent or return electrode. A bipolar lead has two electrode surfaces, separated from each other by a slight spacing. Typically one of these electrodes is formed as a hemispherical electrode at the distal tip of the lead, and the other is a ring electrode, which annularly surrounds the sheath, located a short distance behind the tip electrode.

In most modern cardiac assist devices, the electrode lead is not only used to deliver an appropriate cardiac assist regimen in the form of electrical pulses, but also is used to detect cardiac activity. The detection of cardiac activity can serve many purposes, such as for use in determining whether adjustments to the cardiac assist regimen are necessary, as well as for identifying cardiac rhythm abnormalities which may require immediate preventative action, such as the occurrence of tachycardia or fibrillation. Particularly in the case of a cardioverter or a defibrillator, which is normally passive unless and until tachycardia or fibrillation is detected, it is important not only to reliably detect tachycardia or fibrillation when they occur, but also it is important not to misidentify a non-emergency cardiac rhythm abnormality as tachycardia or fibrillation, since administering the emergency regimen to a healthy heart can possibly create an emergency situation where none exists. Moreover, at least in the case of a defibrillator, unnecessary triggering of the extremely strong defibrillation energy will cause considerable discomfort to the patient.

An electrode lead for a cardiac pacemaker is disclosed in U.S. Pat. No. 5,306,292 which has a distal tip with a number of closely spaced electrodes thereon, with the remainder of the hemispherical surface of the distal tip of the electrode being non-conducting. Circuitry in the pacemaker housing, connected to the respective electrodes via the electrode lead cable, allows the total conductive area and geometry of the distal tip of the electrode lead to be selectively varied, by activating the electrodes in different combinations. For example, the combination of electrodes (i.e. conductive surfaces) at the electrode tip which provides the lowest stimulation threshold can be determined by an autocapture unit, so that energy consumption can be reduced.

Many algorithms are known for analyzing the detected signal wave forms obtained with unipolar and bipolar leads. A prerequisite to the proper functioning of most of these algorithms is that the signal which enters into the algorithm be relatively noise-free. The detected signal, in its raw form, can be corrupted by noise produced by electromagnetic interference in the patient's environment, as well as by muscle activity. Such noise may mimic a fibrillation pattern, for example, particularly in the case of a unipolar lead, but also to a certain extent with a bipolar lead.

Conventional noise-removing techniques involve filtering and other types of signal editing procedures.

After making the incoming signal reasonably noise-free, conventional detection algorithms analyze the signal by undertaking one or more threshold comparisons and/or by analyzing the rate of occurrence of a particular characteristic of the signal (i.e., maxima, minima, zero crossings, etc.) over a given period of time. Comparison of the signal waveform to stored signal templates, respectively representing previously-obtained abnormal signals, is also a known technique. In this manner, a determination is made as to whether the incoming signal represents normal sinus rhythm, a PVC, tachycardia, atrial fibrillation, ventricular fibrillation, etc.

SUMMARY OF THE INVENTION

It is an object of the present invention to provide a method and a circuit for analyzing signals obtained with a cardiac lead having a multi-electrode tip for the purpose of detecting cardiac abnormalities so that remedial action can be taken.

The above object is achieved in accordance with the principles of the present invention in a first embodiment of a method and circuit for analyzing unipolar signals obtained from respective dot-like electrodes disposed at the distal tip of a cardiac lead, which are simultaneously in contact with cardiac tissue, wherein time-related differences between two or more of the unipolar signals are analyzed, and the result of this analysis is used to detect whether a cardiac rhythm abnormality exists. These time-related differences exhibited by the unipolar signals from the dot-like electrodes arise because even though the electrodes are very close together, the speed of the depolarization of the cardiac tissue is not negligible compared to this distance. However, for a specific patient and a specific location of the multi-dot lead, the same time differences between unipolar signals will occur for each heartbeat during normal sinus rhythm. During tachycardia or fibrillation, the speed and direction of the propagating depolarization will be different giving rise to another time difference pattern.

The respective unipolar signals from the dot-like electrodes each exhibit a morphology that is virtually identical from electrode-to-electrode. The fact that the morphologies of the respective unipolar signals are virtually identical is exploited to identify a time shift or time offset of one unipolar signal relative to the other. In one embodiment, this time offset is used to create a delayed difference signal which will be zero or close to zero, during normal sinus rhythm, but exhibit a higher amplitude during tachycardia or fibrillation due to a different depolarization speed and direction. If and when the amplitude of the delayed difference signal, filtered or not, exceeds a threshold level, a cardiac rhythm abnormality is indicated. In another version of the first embodiment of the inventive method and circuit, two or more of the unipolar signals are correlated with each other. Again since the morphologies of two signals is more or less identical except for the shift in time, the time delay between signals can easily be determined using e.g. correlation. When this time difference, as determined by this analysis, deviates too much from what is considered normal it is taken as an indication of an existing cardiac rhythm abnormality.

For a given patient, values for the absolute value of the time shift can be identified and stored which are respectively indicative of tachycardia and fibrillation, so that the two can be distinguished from each other by analysis of the time offset, and thus an appropriate signal can be emitted to initiate different types of appropriate remedial action. Similarly, different values for the correlation result can be obtained and stored, respectively indicative of tachycardia and fibrillation.

In a third version of the first embodiment, the sequence of arrival of the unipolar signals at the respective dot-like electrodes is forming a pattern, and the existence and/or type of cardiac rhythm abnormality is identified dependent on this pattern.

In a second embodiment of the inventive method and circuit, the unipolar signals are surveyed, via a telemetry link, by a physician operating an external programming device, and the physician selects a heartbeat which the physician believes best represents a particular type of cardiac activity, including different types of cardiac abnormalities. The pattern of the sequence of the selected unipolar signal detections is stored as a template, and subsequently obtained unipolar signal detections, as occur during daily activity of the patient, are compared to the stored template, such as by undertaking a pattern recognition. Dependent on the similarity of the subsequent unipolar signals to the stored template, the presence of a cardiac rhythm abnormality is detected.

The dot-like electrodes of the cardiac lead are individually formed of conductive material, and are separated at the surface of the distal tip of the lead by electrically insulating material. The arrangement of the electrode dots can include a centrally disposed electrode dot, with a number of further of electrode dots annularly arranged around the centrally disposed dot. The annularly arranged electrode dots can be located at radially symmetrical positions relative to the centrally disposed dot.

The multiple dots produce respective signals which have features that are slightly offset in time from dot-to-dot so that analysis of these signals can proceed by monitoring the respective offsets. The offsets are represented by relatively easily recognizable wave form features, such as maxima, minima or maximum slew rate.

Each electrode dot preferably has a diameter of 0.5 mm, with the edge-to-edge distances among all of the respective dots being approximately equal. A heart cell is about 0.02 mm wide and approximately 0.1 mm long. This means that one electrode dot will cover a large number of heart cells. When a propagating wave front passes the multiple dots, the coupled heart cells are activated in sequence. This means that the signals registered by each dot electrode in a unipolar fashion will "see" similar pulse shapes (wave forms), but with small time offsets from dot-to-dot. During normal wave propagation, the heart cell excitations follow a relatively synchronized and coordinated pattern. Such a pattern, however, is not present during fibrillation. Even for the small area in contact with the distal tip of the lead, there will be disorganized electrical activity registered by the respective dots. By obtaining individual signals for each electrode dot, and then analyzing these signals as a group, conclusions can be made as to whether normal sinus activity is present, or some type of cardiac abnormality.

In accordance with the invention, one appropriate method for analyzing the signals obtained from the respective electrode dots is to obtain unipolar signals from the respective dots with the cardiac assist housing serving as the ground level. By comparing a difference between respective signals from two dots, a bipolar signal is obtained, although this will be different from a conventional bipolar signal obtained with a tip electrode and a ring electrode configuration. Multiple difference signals are thus available for analysis, and it is also possible to employ one of the electrode dots as a reference, and to refer all of the difference signals to the signal obtained from that one dot.

DESCRIPTION OF THE PREFERRED EMBODIMENTS

Figure 1:
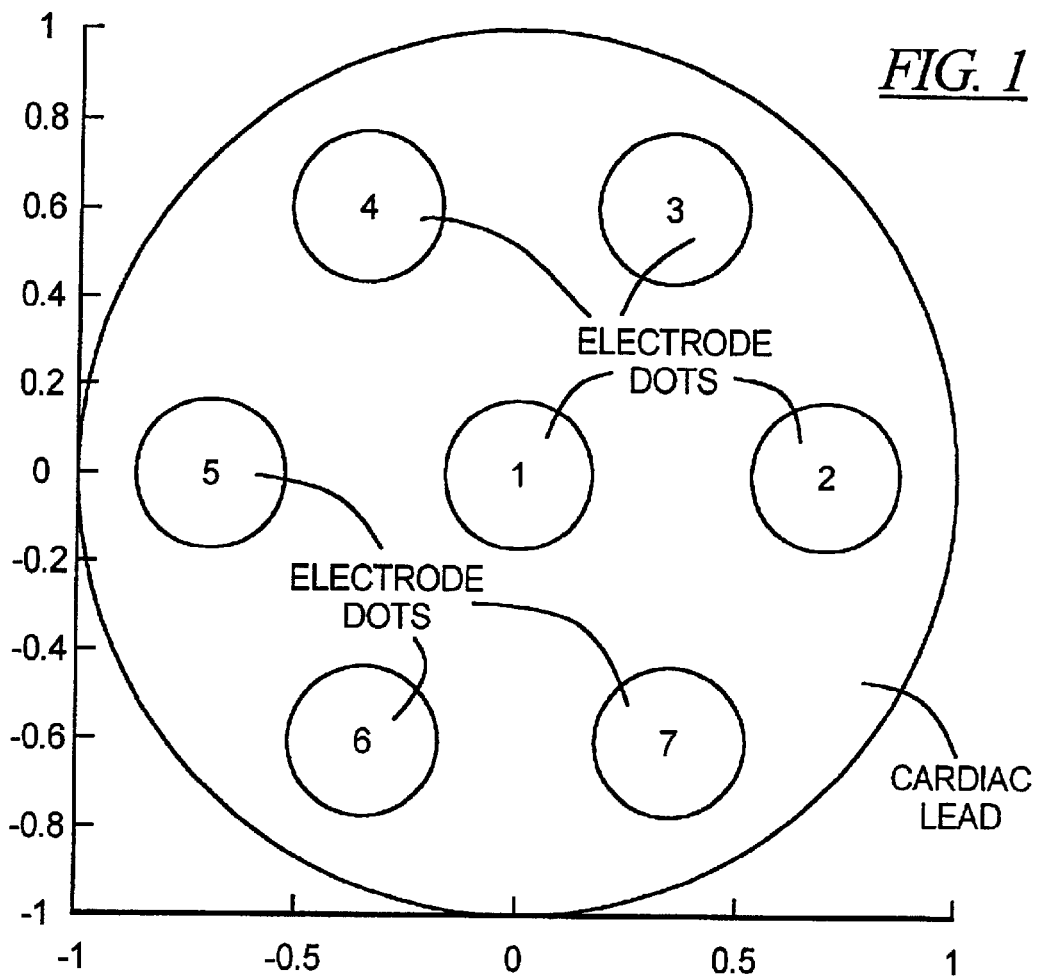
FIG. 1 is a schematic end view of the tip of an electrode lead, in an embodiment heading seven electrode dots, in accordance with the principles of the present invention.

An embodiment of an electrode lead for use with the circuit and method in accordance with the principles of the present invention is shown in FIG. 1, which is a view looking directly at the distal tip (greatly enlarged) of the cardiac lead. As can be seen in FIG. 1, the lead tip has a number of electrode dots distributed thereon, including a centrally disposed electrode dot 1 and a number of other electrode dots arranged relative to the centrally disposed electrode dot 1. In the embodiment of FIG. 1, six other electrode dots 2–7 are shown, for a total of seven electrode dots in the embodiment of FIG. 1. In the embodiment of FIG. 1, the electrode dots 2–7 are shown as being annularly arranged around the centrally disposed electrode dot 1, however, other locations are possible.

The axes shown in FIG. 1 are in arbitrary units and are solely for the purpose of providing a guide as to the relative placement of the electrode dots 1–7. Each electrode dot will have a diameter of approximately 0.5 mm.

The lead tip shown in FIG. 1 is at the distal end of a flexible, implantable electrode lead (schematically shown in FIG. 2), having an opposite end with a plug adapted to be fitted into a cardiac assist device, such as a pacemaker, cardioverter or defibrillator. The lead will contain respective conductors for the electrode dots 1–7, each conductor being insulated from the others and the entire lead being jacketed in an insulating sheath, as is standard. The surface of the electrode tip surrounding the respective electrode dots 1–7 is composed of insulating material, so that the electrode dots are electrically insulated from each other.

In practice, a unipolar signal is obtained from each of the electrode dots 1–7, i.e., seven unipolar signals are obtained. These unipolar signals can be analyzed by time offsets (shifts) differences between the respective unipolar signals from any two of the electrode dots. The reasons why these time effects exist is as follows.

The depolarization of heart cells can be considered as being represented by a propagating wavefront. If the wavefront is assumed to be propagating from right to left in FIG. 1, with the respective unipolar signals from the electrode dots 1–7 being sampled as the wavefront propagates, the wavefront will arrive later at electrode dot 5, for example, than at electrode dot 1, because the distance between the electrode dots is not negligible relative to the propagation speed of the wavefront and the sampling frequency. There will be no offset, for example, between arrival at the wavefront at electrode dots 3 and 7, or arrival of the wavefront at electrode dots 4 and 6.

As an example, assume that the unipolar signal from electrode dot 5 is offset or shifted 1 ms (or 5 samples, if the sampling frequencies is 5 kHz) compared to the unipolar signal from electrode dot 1. The respective waveforms of the unipolar signals from electrode dots 1 and 5 are basically the same in appearance, but as a generalized statement the unipolar signal from the electrode dot 5 will be shifted by 5 samples relative to the unipolar signal from the electrode dot 1. Therefore, the time difference between a sample at a given time t in the unipolar signal obtained from the electrode dot 5, and a sample at time t−5 in the unipolar signal obtained from dot 1, will be 0. If the wavefront comes from a different direction, however, and the difference between the samples at these times in the two unipolar signals is calculated, the difference signal will not be 0.

Thus, for every combination of pairs of electrode dots and direction of propagation of the wavefront, there is a time delay associated with that combination, corresponding to a distinct number of samples. In other words, if it is necessary to delay (shift) one of the unipolar signals by this distinct number of samples before creating a bipolar signal with another unipolar signal, a minimum signal is obtained. The number of samples by which it is necessary to shift one of the unipolar signals relative to the other is determined by calculating the correlation between these two unipolar signals for different time shifts. Shifting one of the signals by the aforementioned distinct number of samples will yield the highest correlation result. Since the calculation of the correlation includes several multiplications, which is time consuming as well as imposing processor demands, alternatively the sum of the absolute differences between the two signals can be calculated. A shift of one signal relative to the other by the aforementioned distinct number of samples will generate the smallest sum of absolute differences.

In order to use the difference signals as an analysis tool for identifying cardiac abnormalities, it must be identified which delay, for a given pair of dots, occurs as a result of normal sinus rhythm, wherein the wavefront is propagating from a specific direction most of the time. If and when fibrillation occurs, due to the chaotic electrical activity of the cardiac tissue, the wavefront will propagate from different directions, and the departure of the delay from the delay which has been identified as representing normal sinus rhythm can be used as an indicator of the onset of fibrillation.

In general, the procedure for analyzing the unipolar signals from a pair of electrode dots is as follows. The delay associated with a pair of electrode dots during normal sinus rhythm is identified, such as by correlation or another suitable technique. This delay can be denoted as delay. During operation of the cardiac assist device, a delayed difference signal is continuously calculated, such as $x1(t)-x2(t-d)$, instead of the undelayed difference signal $x1(t)-x2(t)$, wherein x1 and x2 represent the respective unipolar signals from two electrode dots in the pair under consideration. If the delayed difference signal, with appropriate filtering, if necessary, is larger than a threshold value, an episode of non-sinus rhythm is assumed to exist. The threshold value can be a predetermined value or can be adapted as data are accumulated.

As noted above, what is really being detected using the electrode lead shown in FIG. 1 is whether the propagating wavefront is arriving from a direction different from that which occurs during normal sinus rhythm. This change in direction, in addition to arising from an episode of fibrillation, could arise due to a premature ventricular contraction (PVC), or due to slight dislodgement of the lead. As explained below, by appropriate filtering and/or decision algorithms, the false detection of a PVC as ventricular-fibrillation can be eliminated. The probability of lead dislodgement becomes negligible after a period of time following implantation.

It is recommended to periodically reinitialize the delay factor, i.e. to re-identify the delay associated with normal sinus rhythm at predetermined intervals, or when the delayed difference signal has slowly changed by more than a predetermined percentage.

Figure 2:
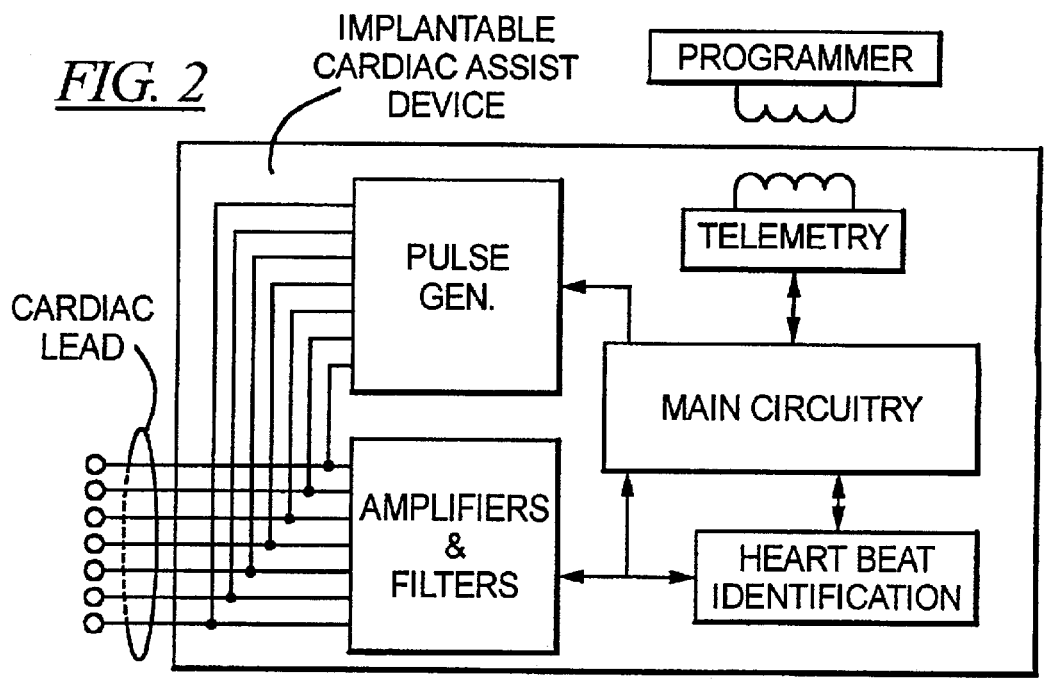
FIG. 2 is a block diagram showing the basic components of an implantable cardiac assist device, constructed and operating in accordance with the principles of the present invention.
Figure 3:
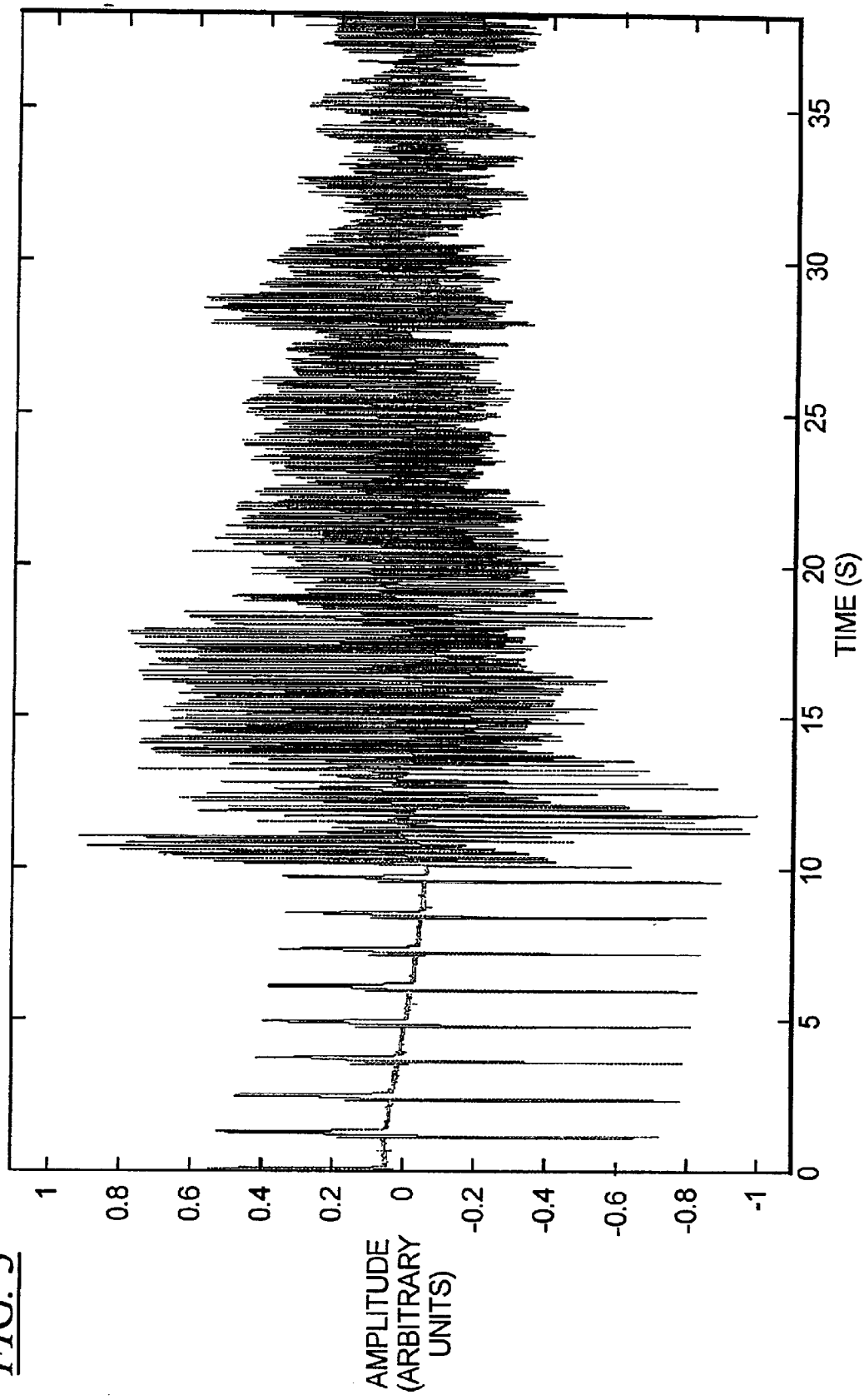
FIG. 3 illustrates the unipolar signal from the centrally disposed electrode dot in the embodiment of FIG. 1.

The basic components of an implantable cardiac assist device in accordance with the invention are shown in FIG. 2. The implantable cardiac assist device can be a pacemaker, a cardioverter or a defibrillator, for example.

The implantable cardiac assist device has an input stage including amplifiers and filters, to which respective conductors, together forming a cardiac lead, from the electrode dots 1–7 are supplied. The unipolar signals from the electrode dots 1–7 are supplied to a heart beat identification stage as well as to main circuitry in the cardiac assist device. The functioning of the heartbeat identification stage will be described below, in several embodiments. The main circuitry is whatever type of circuitry is appropriate for the cardiac assist device, and can include pacing logic if the device is a pacemaker, or defibrillation circuitry if the device is a defibrillator. The appropriate cardiac assist therapy is generated in a known manner by the main circuitry and is delivered to the patient either through the aforementioned electrode lead or another appropriately designed electrode lead. The main circuitry, therefore, is conventional, except that it responds to a heartbeat identification signal produced in accordance with the invention.

The main circuitry is also in communication with a telemetry unit, which wirelessly communicates with an external programmer in a known manner for reading out patient data and for making changes in the operating parameters of the implantable cardiac assist device, as needed.

Based on the unipolar signals from dots 1, 2, 3 and 4, the time difference between dots 1 and 2, dots 1 and 3 and dots 1 and 4 as a function of time is calculated using correlation. A portion of a predetermined length, i.e., the window length, of the signals from dot 1 and dot 2 is selected. The window length may be one second, for example. The correlation between the two signal portions of the respective unipolar signals is then calculated and stored. The signal from dot 2 is then shifted by one sample compared to the signal from dot 1, and the correlation is again calculated and stored. The window is then shifted two samples from the original position, and a new correlation is calculated and stored. This process is repeated for a predetermined number of shifts of the window, both positive and negative. The shift producing the highest correlation is the delay between the two dots in question. As described above, alternatively the sum of squares of the signal differences can be used, in order to avoid the time and complications associated with correlation calculations. In this alternative embodiment, a minimum should be sought.

Figure 4:
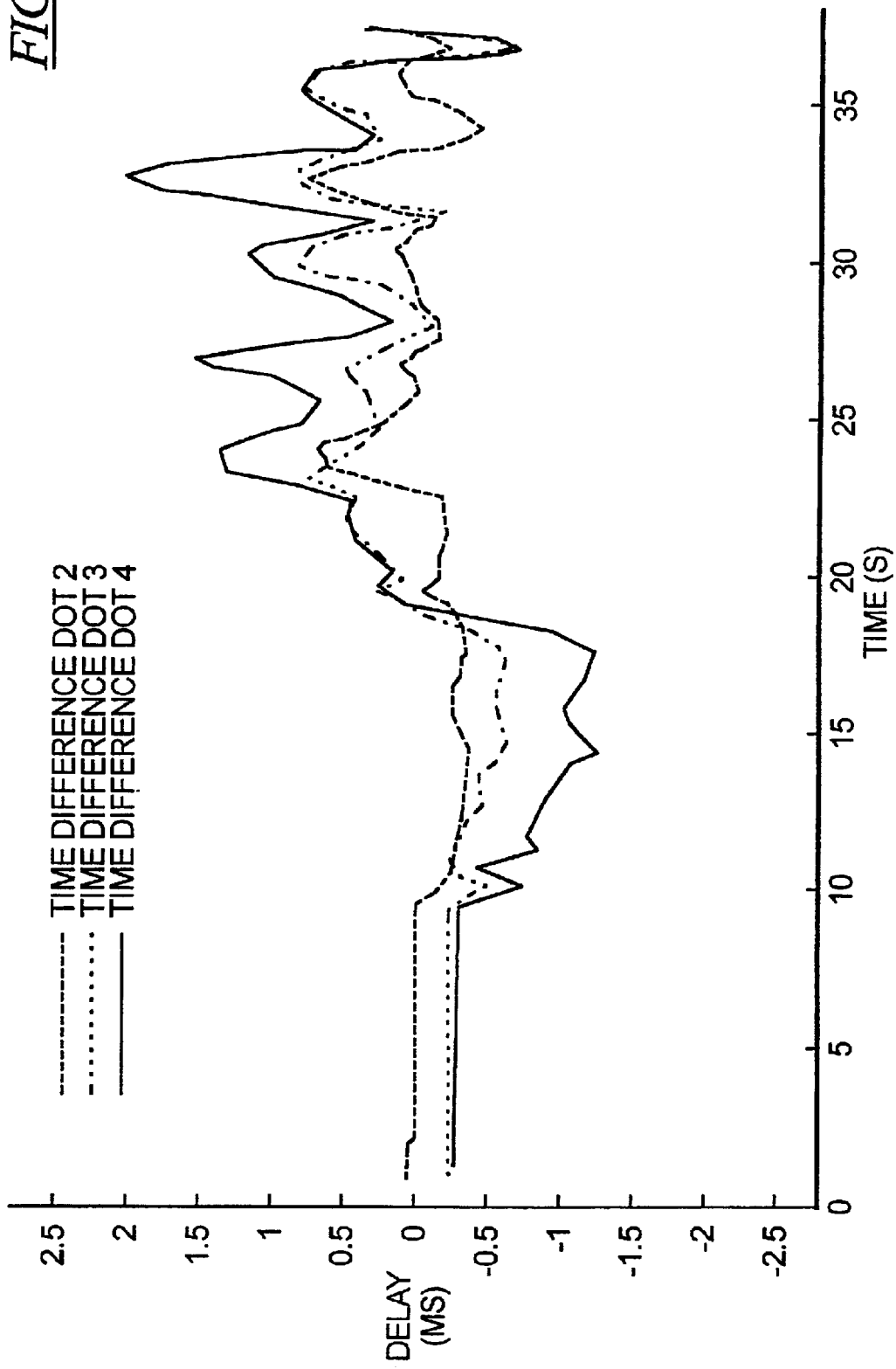
FIG. 4 illustrates respective difference signals between the centrally disposed electrode dot and other electrode dots, in accordance with the invention.

As time progresses, the process is repeated, so that a plot of the time difference compared to the center dot arises as a function of time. This is shown in FIG. 4. The same algorithm as described above was used for determining the time difference between dots 1 and 3 and dots 1 and 4.

As can be seen in FIG. 4, the time delay or time difference is constant during normal sinus rhythm and varies during fibrillation. A varying time difference between a pair of dots is thus a major indication of fibrillation. The time difference signal, after filtering, differentiation or some other manipulation, can be employed in combination with a threshold level to detect fibrillation.

Figure 5:
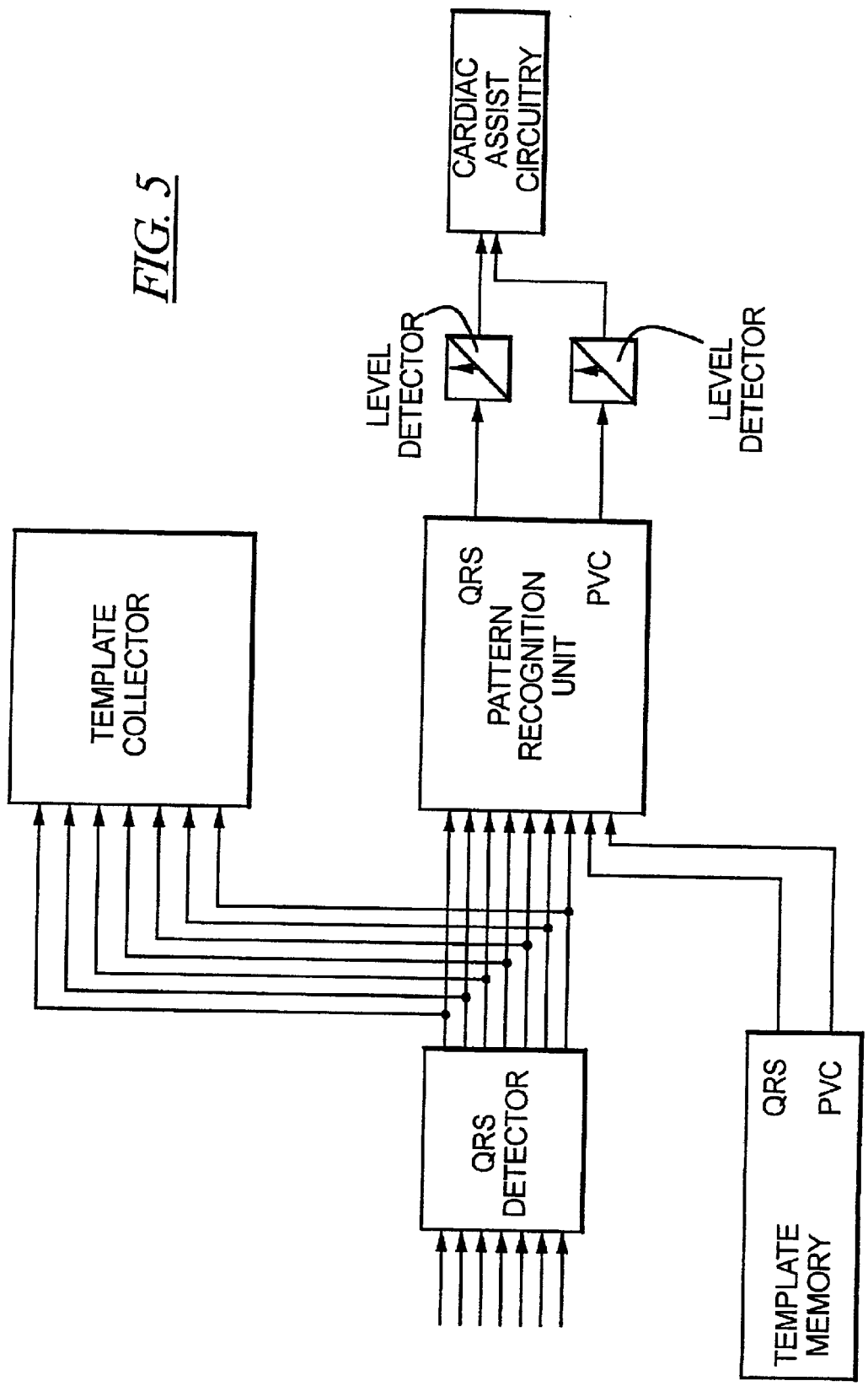
FIG. 5 is a block diagram of an embodiment for the block labeled "Heart Beat Identification" in FIG. 2.

An embodiment of the heartbeat identification stage of FIG. 2 is shown in FIG. 5. In this embodiment, signals obtained from the electrode dot lead are supplied to a QRS detector. These signals are supplied from the QRS detector to a pattern recognition unit as well as to a template collector. The template collector, through the main circuitry and the telemetry link, is in communication with the external programmer. Signals from the electrode dot lead continuously arrive via the QRS detector at the template collector and are fed into a shift register. Via the telemetry link, a physician who is monitoring the heart activity can freeze the contents of the shift register when a representative beat of the type which is intended to be stored as a template is present. Otherwise, the signals proceed through the shift register and are not stored or prevented from entering said shift register. When the physician recognizes a signal displayed at the programmer of the type which the physician wishes to store, the physician operates the programmer to cause that signal to be stored in the template memory.

Figure 6:
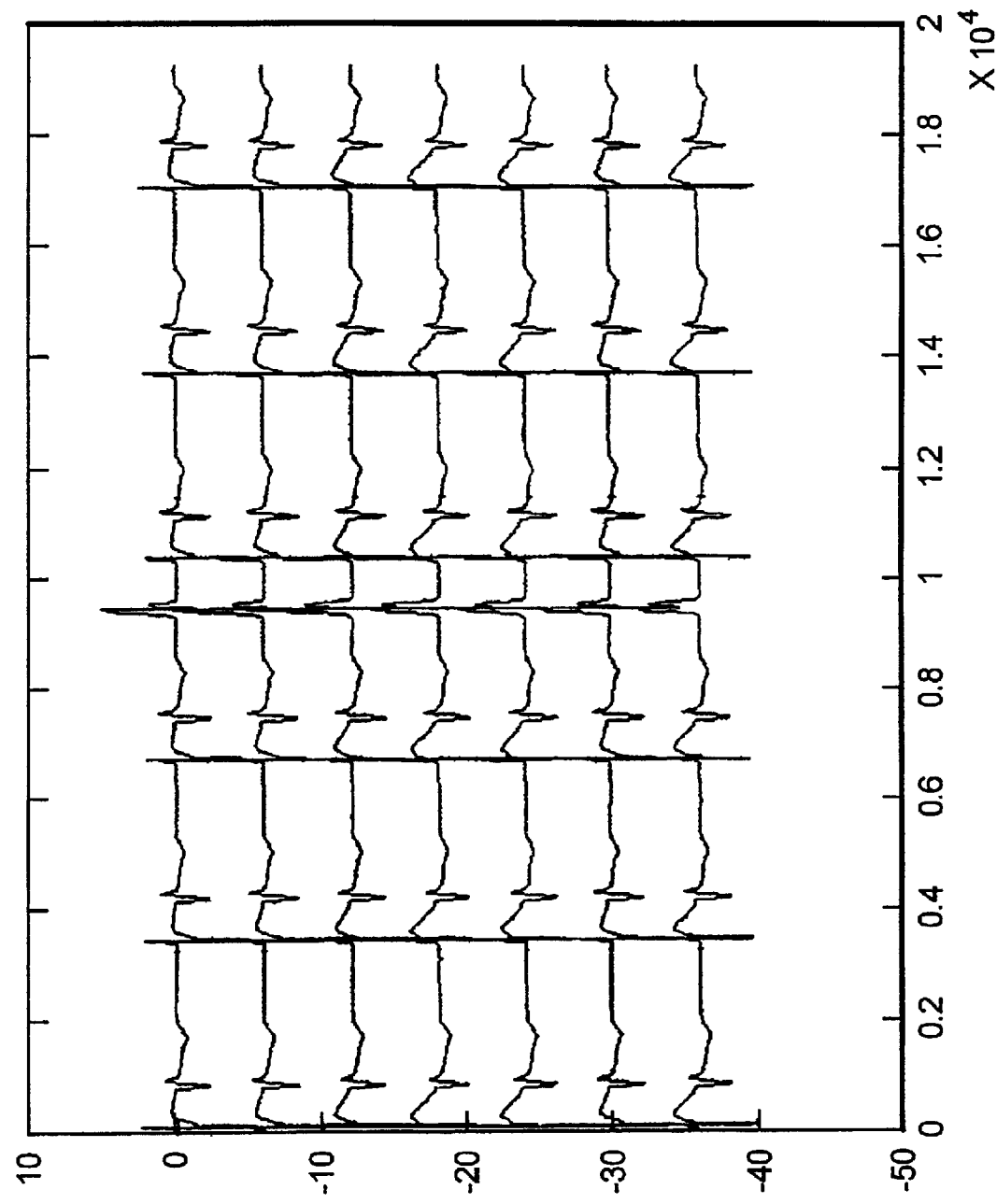
FIG. 6 illustrates input signals from the electrode dots in the embodiment of FIG. 1.
Figure 7:
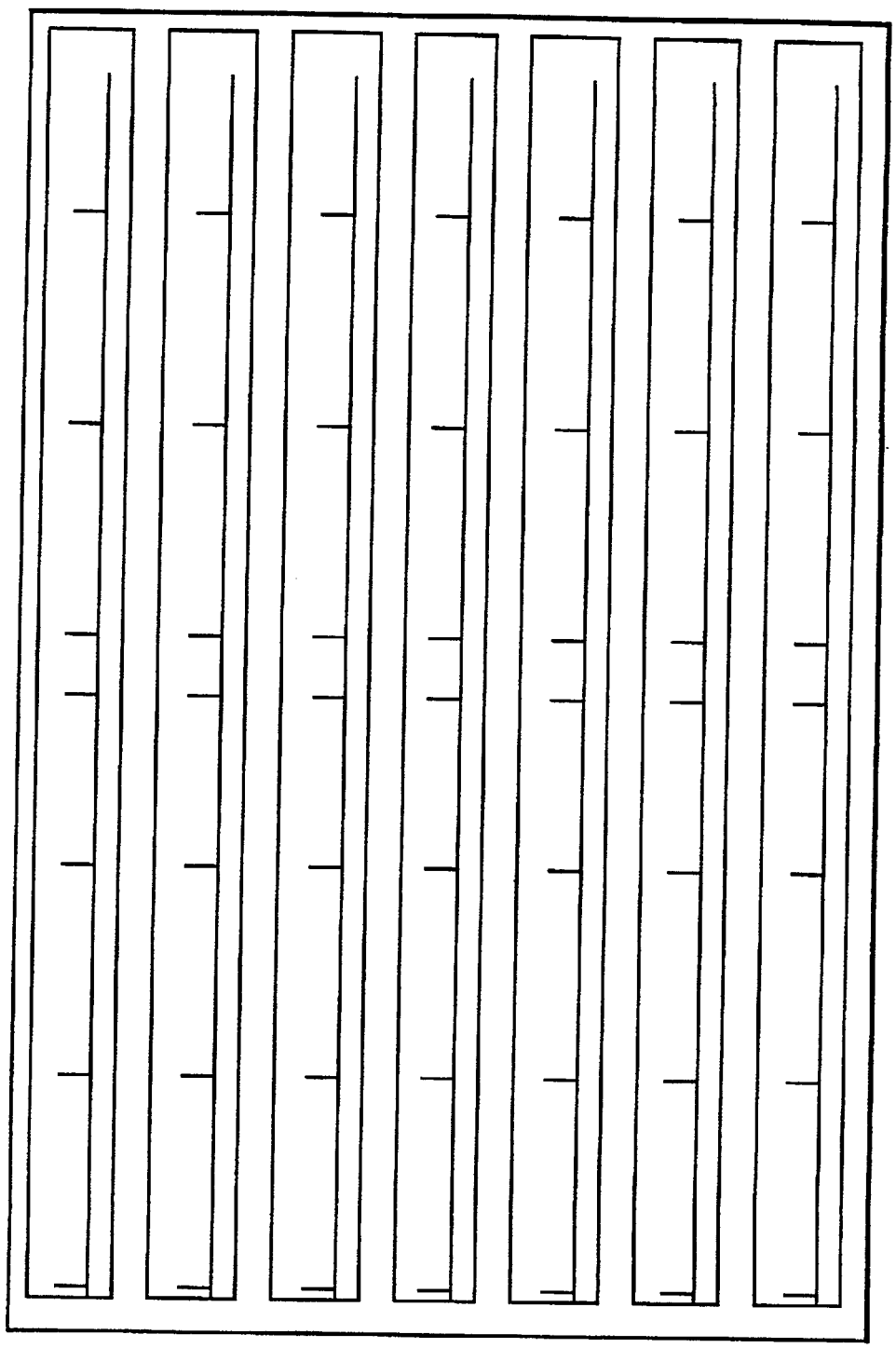
FIG. 7 illustrates the output pulses for the intracardial signals shown in FIG. 6.
Figure 9:
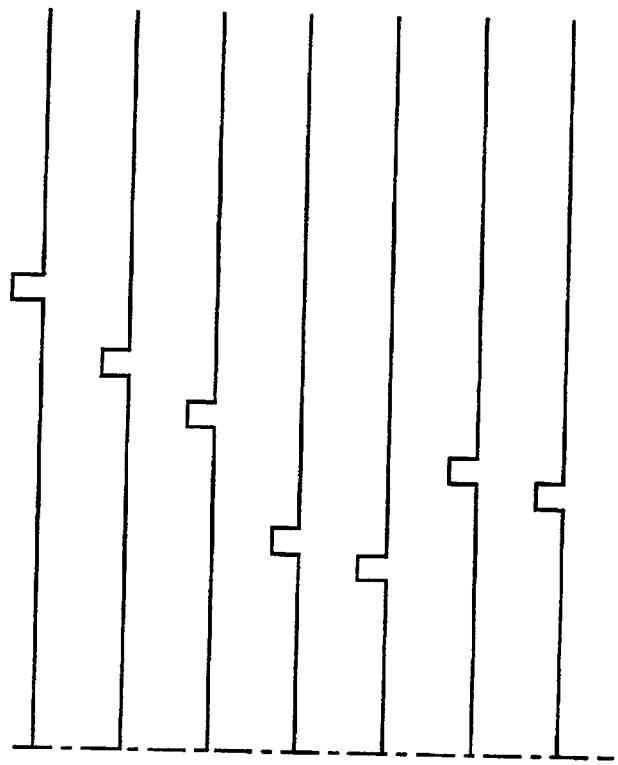
FIG. 9 illustrates the detector pulse pattern for the fifth beat in FIG. 7.
Figure 8:
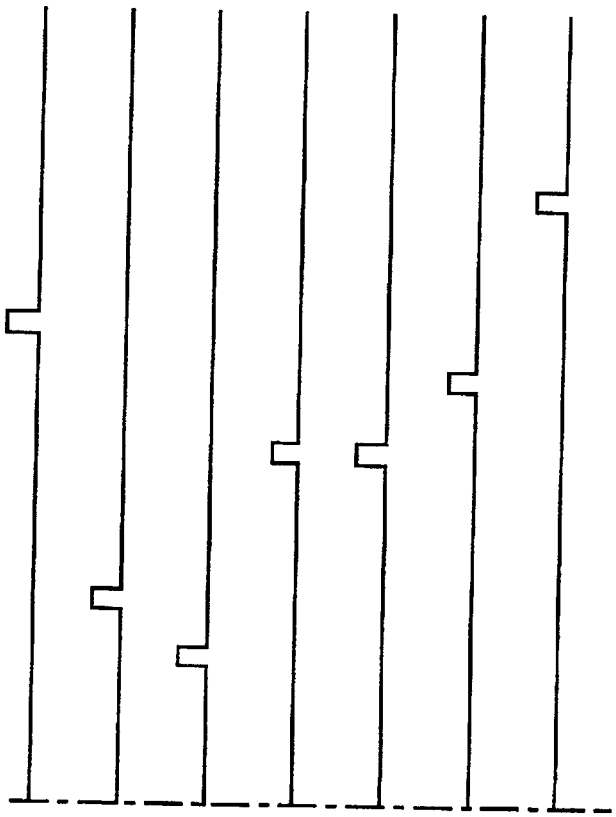
FIG. 8 illustrates the detector pulse pattern for the fourth beat in FIG. 7.

As an example, input signals from the electrode dots 1–7 obtained during the occurrence of a PVC are shown in FIG. 6. The PVC occurs in the middle of FIG. 6. FIG. 7 shows the detector pulses from the output of the QRS detector for the signals shown in FIG. 6. There are no distinguishable patterns which are visually apparent from FIG. 7, but if pulses from the signals from the electrode dots 1–7 are obtained and analyzed as described above, reliable detection can be made as shown in FIGS. 8 and 9. The detector pulse pattern for the fourth beat in the signals shown in FIG. 6 is shown in FIG. 8. The pulse pattern for the next beat (the fifth beat), which is a normal beat, is shown in FIG. 9. When analyzed in this manner, the difference is readily apparent.

Figure 10:
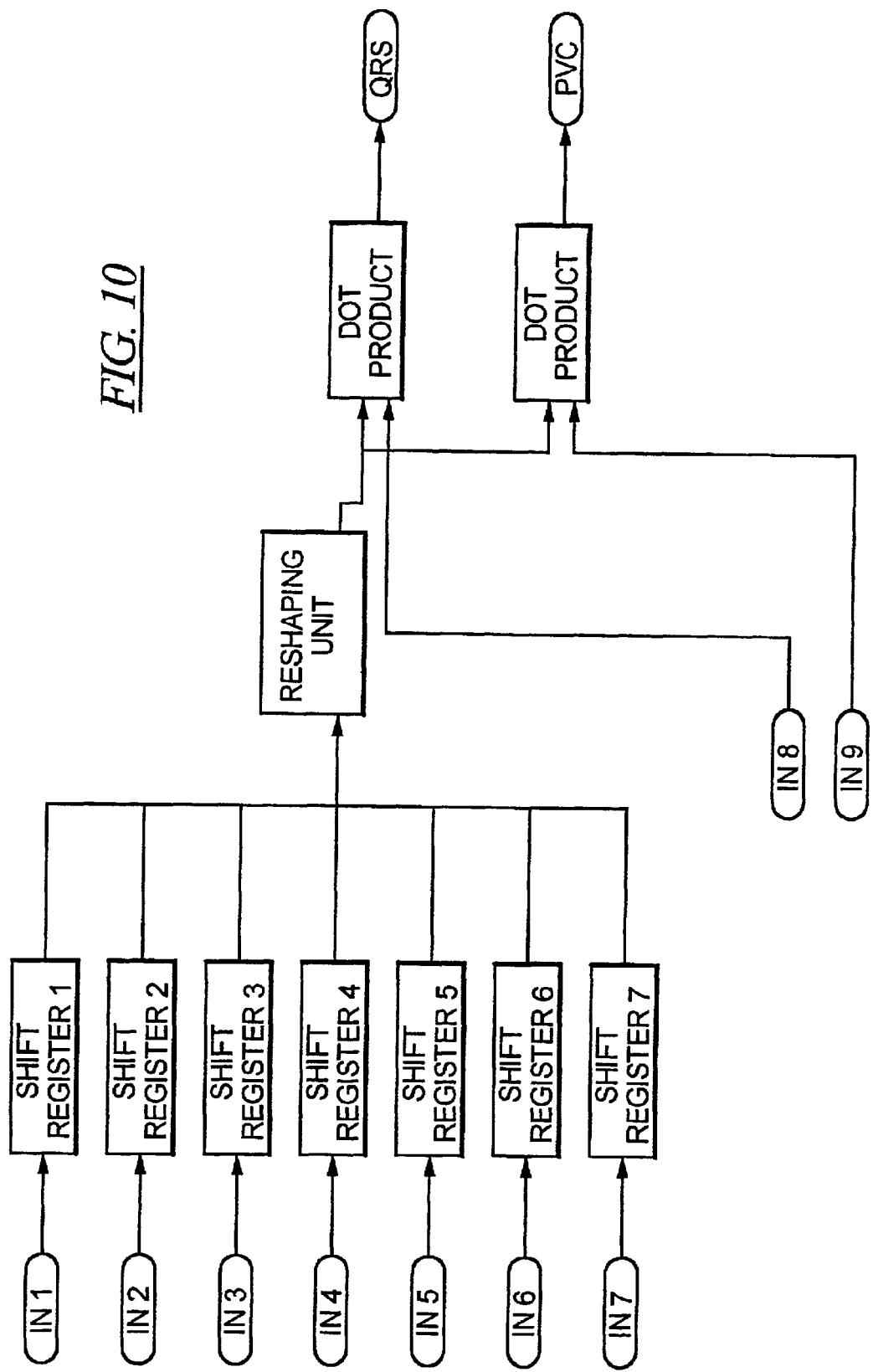
FIG. 10 is a block diagram of an embodiment of the pattern recognition unit of FIG. 5.

Details of an embodiment for the pattern recognition block of FIG. 5 are shown in FIG. 10. The input signals IN1–IN7 are the pulses of the type shown in FIGS. 8 and 9. These pulses are respectively supplied to shift register 1–shift register 7 and the outputs of these shift registers are supplied to a reshaping unit. The pattern recognition unit is also supplied with two further inputs IN8 and IN9, which respectively represent the QRS template and the PVC template, stored in the template memory. The clock signal (not shown) for operating these shift registers is the same as was used to generate the stored templates, i.e., the clock signal that was used to feed the signals from the QRS detector to the template collector. This is necessary so that a direct correspondence will exist between the now-detected signals and the stored templates.

The output of the reshaping unit is supplied to each of two dot product forming stages ("dot product" meaning the vector dot product). These dot product forming stages are respectively are supplied with the QRS and PVC templates. By forming the respective dot product of these templates, in vector form, with the vector formed by the inputs IN1–IN7 in the reshaping unit, an indication of whether normal QRS activity is present or whether a PVC is present is obtained.

Instead of using a dot product, other possible techniques are convolution and cross-correlation.

Figure 11:
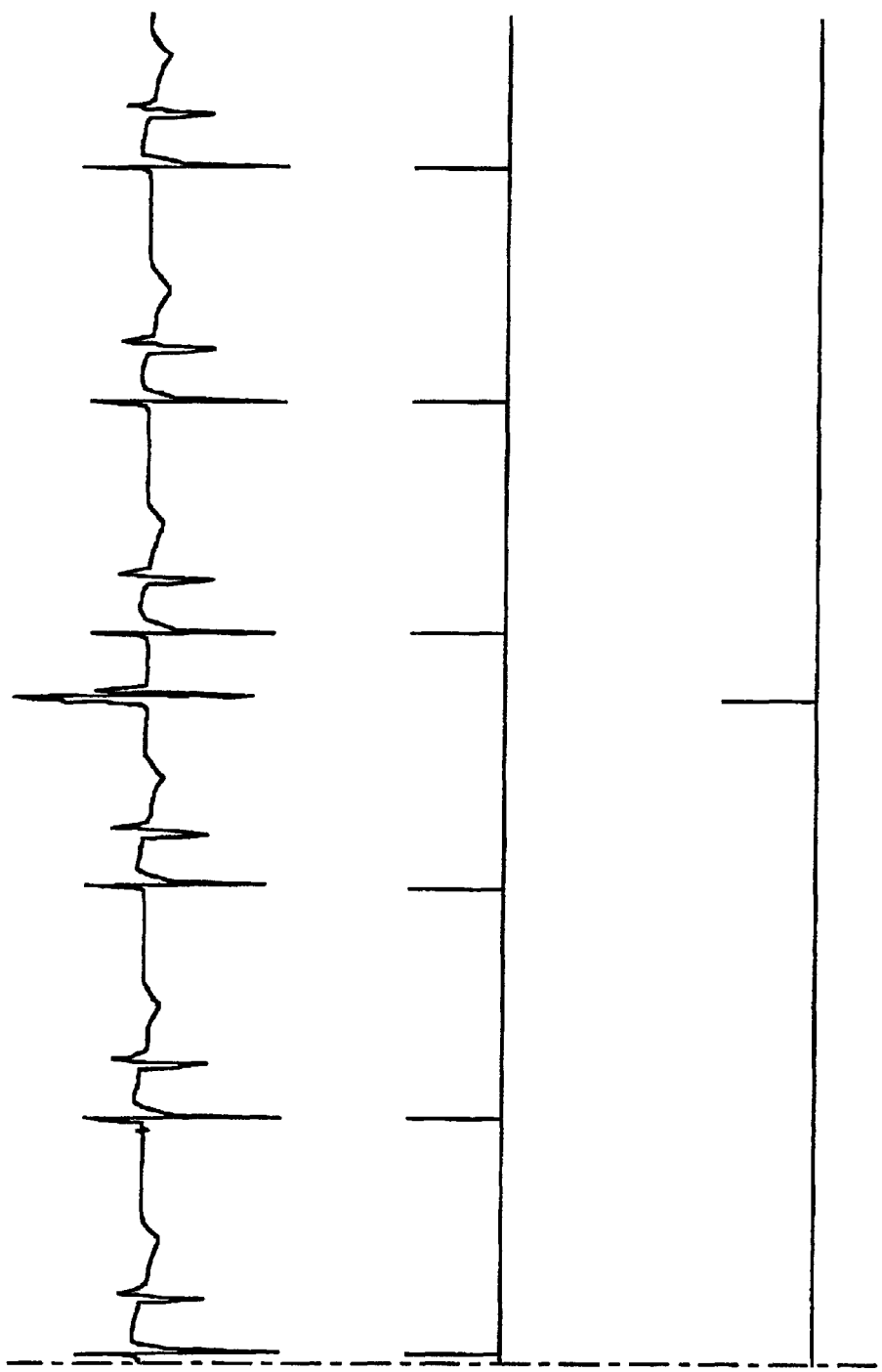
FIG. 11 illustrates results from the pattern recognition unit, and one input signal.

FIG. 11 shows representative signals in the circuit shown in FIG. 10. The top signal is one of the input signals to the QRS detector, the middle signal is the output of the QRS level detector, and the bottom signal is the output of the PVC level detector.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for detecting cardiac rhythm abnormality, comprising the steps of:

providing a plurality of electrodes at a tip of a cardiac lead, which are electrically separated from each other;

placing said tip of said cardiac lead in contact with cardiac tissue so that all of said electrodes are simultaneously in substantially fixed contact with said cardiac tissue;

obtaining individual unipolar electrical signals from said cardiac tissue respectively via said electrodes, said unipolar signals exhibiting a time relationship relative to each other;

defining a time window;

sampling one of said unipolar signals and another of said unipolar signals;

correlating samples in said time window of said one of said unipolar signals with samples in said time window of said another of said unipolar signals to obtain a first correlation result;

successively shifting said time window by one sample and, after each shift, again correlating the samples of said one of said unipolar signals in said time window with the samples of said another of said unipolar signals in said time window, to obtain a plurality of successive correlation results;

identifying a time offset between said one of said unipolar signals and said another of said unipolar signals by a number of samples associated with a shift of said time window which produced a highest correlation result among said first and successive correlation results; and generating a signal indicating a cardiac rhythm abnormality dependent on said time offset.

2. A method as claimed in claim 1 comprising forming individual electrodes in said plurality of electrodes as respective dot-like electrodes.

3. A method as claimed in claim 1 comprising arranging said plurality of electrodes at said one end of said cardiac lead with respective spacings between the electrodes which are substantially equal.

4. A method as claimed in claim 1 comprising disposing one of said electrodes at a center of said one end of said cardiac lead, and arranging a remainder of said electrodes symmetrically relative to said one of said electrodes.

5. A method as claimed in claim 1 comprising disposing one of said electrodes at a center of said one end of said cardiac lead, and arranging a remainder of said electrodes radially symmetrically relative to said one of said electrodes.

6. A method as claimed in claim 1 wherein the step of obtaining individual unipolar electrical signals comprises obtaining a plurality of individual unipolar electrical signals from said cardiac tissue respectively via said electrodes with one unipolar signal being obtained for each electrode, making the plurality of unipolar signals equal to the plurality of electrodes.

7. A method for detecting cardiac rhythm abnormality, comprising the steps of:
   providing a plurality of electrodes at a tip of a cardiac lead, which are electrically separated from each other;
   placing said tip of said cardiac lead in contact with cardiac tissue so that all of said electrodes are simultaneously in substantially fixed contact with said cardiac tissue;
   obtaining detections of individual unipolar electrical signals from said cardiac tissue respectively via said electrodes;
   selecting a heartbeat representing a cardiac rhythm abnormality;
   storing a detection pattern for the individual unipolar electrical signals obtained during said heartbeat as a template; and
   subsequently obtaining further detections of individual unipolar electrical signals from said cardiac tissue respectively via said electrodes and comparing said subsequently obtained detections of unipolar signals to said stored template to obtain a comparison result, and generating a signal indicating a cardiac rhythm abnormality dependent on said comparison result.

8. A method as claimed in claim 7 wherein the step of comparing said subsequently obtained detections of unipolar signals to said template comprises conducting a pattern recognition between said subsequently obtained detections of unipolar signals and said template.

9. A method as claimed in claim 7 wherein the step of selecting a heartbeat representing a cardiac rhythm abnormality comprises selecting a plurality of different heartbeats respectively representing different cardiac rhythm abnormalities, and wherein the step of storing a detection pattern comprises storing a plurality of respective detection patterns for the individual unipolar electrical signals respectively obtained during said different heartbeats, as a plurality of templates respectively for said different cardiac rhythm abnormalities, and wherein the step of comparing said subsequently obtained detections of unipolar signals to said stored template comprises comparing said subsequently obtained detections of unipolar signals to the plurality of stored templates to obtain a comparison result indicating which of said templates said subsequently obtained detections of unipolar signals most closely resembles, and generating a signal indicating the respective cardiac rhythm abnormality, from among said plurality of cardiac rhythm abnormalities, dependent on said comparison result.

10. A method as claimed in claim 7 comprising forming individual electrodes in said plurality of electrodes as respective dot-like electrodes.

11. A method as claimed in claim 7 comprising arranging said plurality of electrodes at said one end of said cardiac lead with respective spacings between the electrodes which are substantially equal.

12. A method as claimed in claim 7 comprising disposing one of said electrodes at a center of said one end of said cardiac lead, and arranging a remainder of said electrodes symmetrically relative to said one of said electrodes.

13. A method as claimed in claim 7 comprising disposing one of said electrodes at a center of said one end of said cardiac lead, and arranging a remainder of said electrodes radially symmetrically relative to said one of said electrodes.

14. A cardiac rhythm abnormality detector comprising:
   a cardiac lead having a plurality of electrodes at a tip of said cardiac lead, which are electrically separated from each other, said tip of said cardiac lead being adapted for placement in contact with cardiac tissue so that all of said electrodes are simultaneously in substantially fixed contact with said cardiac tissue;
   a QRS detector connected to said cardiac lead which obtains individual unipolar electrical signals from said cardiac tissue respectively via said electrodes, said unipolar signals exhibiting a time relationship relative to each other; and
   an evaluation circuit that correlates said one of said unipolar signals with another of said unipolar signals by defining a time window, sampling said one of said unipolar signals and said another of said unipolar signals, correlating samples in said time window of said one of said unipolar signals with samples in said time window of said another of said unipolar signals to obtain a first correlation result, successively shifting said time window by one sample and, after each shift, again correlating the samples of said one of said unipolar signals in said time window with the samples of said another of said unipolar signals in said time window, to obtain a plurality of successive correlation results, identifying a time offset between said one of said unipolar signals and said another of said unipolar signals by a number of samples associated with a shift of said time window which produced a highest correlation result among said first and successive correlation results, and said evaluation circuit generates said signal indicating a cardiac rhythm abnormality dependent on said time offset.

15. A cardiac rhythm abnormality detector as claimed in claim 14 wherein said plurality of electrodes are respective dot-like electrodes.

16. A cardiac rhythm abnormality detector as claimed in claim 14 wherein said plurality of electrodes at said tip of said cardiac lead are disposed with respective spacings between the electrodes which are substantially equal.

17. A cardiac rhythm abnormality detector as claimed in claim 14 wherein one of said electrodes is disposed at a center of said tip of said cardiac lead, with a remainder of said electrodes disposed symmetrically relative to said one of said electrodes.

18. A cardiac rhythm abnormality detector as claimed in claim 17 wherein said remainder of said electrodes are disposed radially symmetrically relative to said one of said electrodes.

19. A cardiac rhythm abnormality detector as claimed in claim 14 wherein said QRS detector is connected to said electrode lead for obtaining a plurality of said individual unipolar electrical signals from said cardiac tissue respectively via said electrodes, with one unipolar signal being obtained for each electrode, making the plurality of unipolar signals equal to the plurality of electrodes.

20. A cardiac rhythm abnormality detector, comprising:
a cardiac lead having a plurality of electrodes at a tip of said cardiac lead, which is electrically separated from each other, said tip of said cardiac lead being adapted for placement contact with cardiac tissue so that all of said electrodes are simultaneously in substantially fixed contact with said cardiac tissue;
a QRS detector connected to said cardiac lead which obtains individual unipolar electrical signals from said cardiac tissue respectively via said electrodes;
an extracorporeal programming device which allows selection of a heartbeat representing a cardiac rhythm abnormality by taking detections from the individual unipolar signals into account;
a template memory in which the detection pattern obtained at said cardiac rhythm abnormally is stored as a template;
said QRS detector subsequently obtaining further individual unipolar electrical signals from said cardiac tissue respectively via said electrodes; and
an evaluation circuit which compares said subsequently obtained unipolar signals to said stored template to obtain a comparison result, and generates a signal indicating a cardiac rhythm abnormality dependent on said comparison result.

21. A cardiac rhythm abnormality detector as claimed in claim 20 wherein said evaluation circuit compares said subsequently obtained unipolar signals to said template comprises conducting a pattern recognition between said subsequently obtained unipolar signals and said template.

22. A cardiac rhythm abnormality detector as claimed in claim 20 wherein said extracorporeal programming device allows selection of a plurality of different heartbeats respectively representing different cardiac rhythm abnormalities by taking detections from the individual unipolar signals into account, and wherein said template memory stores a plurality of detection patterns respectively obtained at said different cardiac rhythm abnormalities, and wherein said evaluation circuit compares said subsequently obtained unipolar signals to said plurality of stored templates to obtain a comparison result indicating which of said stored templates said subsequently obtained unipolar signals most closely resemble, and wherein said evaluation circuit generates a signal indicating a type of cardiac rhythm abnormality, from among said plurality of cardiac rhythm abnormalities, dependent on said comparison result.

23. A cardiac rhythm abnormality detector as claimed in claim 20 comprising forming individual electrodes in said plurality of electrodes as respective dot-like electrodes.

24. A cardiac rhythm abnormality detector as claimed in claim 20 comprising arranging said plurality of electrodes at said one end of said cardiac lead with respective spacings between the electrodes which are substantially equal.

25. A cardiac rhythm abnormality detector as claimed in claim 20 comprising disposing one of said electrodes at a center of said one end of said cardiac lead, and arranging a remainder of said electrodes symmetrically relative to said one of said electrodes.

26. A cardiac rhythm abnormality detector as claimed in claim 20 comprising disposing one of said electrodes at a center of said one end of said cardiac lead, and arranging a remainder of said electrodes radially symmetrically relative to said one of said electrodes.

27. An implantable cardiac assist device comprising:
a cardiac lead having a plurality of electrodes at a tip of said cardiac lead, which are electrically separated from each other, said tip of said cardiac lead being adapted for placement in contact with cardiac tissue so that all of said electrodes are simultaneously in substantially fixed contact with said cardiac tissue;
an electrical stimulation generator connected to said cardiac lead for delivering electrical stimulation to said cardiac tissue via said plurality of electrodes;
a control unit connected to said electrical stimulation generator;
a QRS detector which obtains individual unipolar electrical signals from said cardiac tissue respectively via said electrodes, said unipolar signals exhibiting a time relationship relative to each other; and
an evaluation circuit that correlates said one of said unipolar signals with another of said unipolar signals by defining a time window, sampling said one of said unipolar signals and said another of said unipolar signals, correlating samples in said time window of said one of said unipolar signals with samples in said time window of said another of said unipolar signals to obtain a first correlation result, successively shifting said time window by one sample and, after each shift, again correlating the samples of said one of said unipolar signals in said time window with the samples of said another of said unipolar signals in said time window, to obtain a plurality of successive correlation results, identifying a time offset between said one of said unipolar signals and said another of said unipolar signals by a number of samples associated with a shift of said time window which produced a highest correlation result among said first and successive correlation results, and said evaluation circuit generates said signal indicating a cardiac rhythm abnormality dependent on said time offset.

28. An implantable cardiac assist device as claimed in claim 27 wherein said plurality of electrodes are respective dot-like electrodes.

29. An implantable cardiac assist device as claimed in claim 27 wherein said plurality of electrodes at said tip of said cardiac lead are disposed with respective spacings between the electrodes which are substantially equal.

30. An implantable cardiac assist device as claimed in claim 27 wherein one of said electrodes is disposed at a center of said tip of said cardiac lead, with a remainder of said electrodes disposed symmetrically relative to said one of said electrodes.

31. An implantable cardiac assist device as claimed in claim 27 wherein said remainder of said electrodes are disposed radially symmetrically relative to said one of said electrodes.

32. An implantable cardiac assist device comprising:
a cardiac lead having a plurality of electrodes at a tip of said cardiac lead, which are electrically separated from each other, said tip of said cardiac lead being adapted for placement in contact with cardiac tissue so that all of said electrodes are simultaneously in substantially fixed contact with said cardiac tissue;
an electrical stimulation generator connected to said cardiac lead for delivering electrical stimulation to said cardiac tissue via said plurality of electrodes;
a control unit connected to said electrical stimulation generator;
a QRS detector which obtains individual unipolar electrical signals from said cardiac tissue respectively via said electrodes, said unipolar signals exhibiting a time relationship relative to each other; and an extracorporeal programmer which allows selection of a heartbeat representing a cardiac rhythm abnormality by taking detections from the individual unipolar signals into account;

a template memory in which the detection pattern obtained at said cardiac rhythm abnormality is stored as a template;

said QRS detector subsequently obtaining further individual unipolar electrical signals from said cardiac tissue respectively via said electrodes; and an evaluation circuit which compares said subsequently obtained unipolar signals to said stored template to obtain a comparison result, and which generates a signal indicating a cardiac rhythm abnormality dependent on said comparison result to said control unit for triggering delivery of said electrical stimulation by said electrical stimulation generator.

33. An implantable cardiac assist device as claimed in claim 32 wherein said evaluation circuit compares said subsequently obtained unipolar signals to said template comprises conducting a pattern recognition between at least one of said subsequently obtained unipolar signals and said template.

34. An implantable cardiac assist device as claimed in claim 32 wherein said extracorporeal programming device allows selection of a plurality of different heartbeats respectively representing different cardiac rhythm abnormalities by taking detections from the individual unipolar signals into account, and wherein said template memory stores a plurality of detection patterns respectively obtained at said different cardiac rhythm abnormalities, and wherein said evaluation circuit compares said subsequently obtained unipolar signals to said plurality of stored templates to obtain a comparison result indicating which of said stored templates said subsequently obtained unipolar signals most closely resemble, and wherein said evaluation circuit generates a signal indicating a type of cardiac rhythm abnormality, from among said plurality of cardiac rhythm abnormalities, dependent on said comparison result.

35. An implantable cardiac assist device as claimed in claim 32 comprising forming individual electrodes in said plurality of electrodes as respective dot-like electrodes.

36. An implantable cardiac assist device as claimed in claim 32 comprising arranging said plurality of electrodes at said one end of said cardiac lead with respective spacings between the electrodes which are substantially equal.

37. An implantable cardiac assist device as claimed in claim 32 comprising disposing one of said electrodes at a center of said one end of said cardiac lead, and arranging a remainder of said electrodes symmetrically relative to said one of said electrodes.

38. An implantable cardiac assist device as claimed in claim 32 comprising disposing one of said electrodes at a center of said one end of said cardiac lead, and arranging a remainder of said electrodes radially symmetrically relative to said one of said electrodes.

* * * * *